United States Patent [19]
Wood et al.

[11] Patent Number: 5,462,583
[45] Date of Patent: Oct. 31, 1995

[54] ABSORPTION PROCESS WITHOUT EXTERNAL SOLVENT

[75] Inventors: Glenn C. Wood, Houston; Yuv R. Mehra, The Woodlands, both of Tex.

[73] Assignee: Advanced Extraction Technologies, Inc., Houston, Tex.

[21] Appl. No.: 206,420

[22] Filed: Mar. 4, 1994

[51] Int. Cl.⁶ ................................................ B01D 47/14
[52] U.S. Cl. .................... 95/192; 62/20; 95/96; 95/143; 95/208; 95/230; 95/237; 585/809
[58] Field of Search ............................ 95/187, 192, 208, 95/141, 127–130, 143–147, 230–232, 237–240, 96; 62/17, 20; 585/809, 867

[56] References Cited

U.S. PATENT DOCUMENTS

| | | | |
|---|---|---|---|
| 3,633,371 | 1/1972 | Davison | 62/17 |
| 4,035,167 | 7/1977 | Starks | 95/173 |
| 4,421,535 | 12/1983 | Mehra | 62/17 |
| 4,526,594 | 7/1985 | Mehra | 62/17 |
| 4,578,094 | 3/1986 | Mehra | 62/17 |
| 4,617,038 | 10/1986 | Mehra | 62/17 |
| 4,623,371 | 11/1986 | Mehra | 62/17 |
| 4,680,042 | 7/1987 | Mehra | 62/17 |
| 4,692,179 | 9/1987 | Mehra | 62/17 |
| 4,695,672 | 9/1987 | Bunting | 585/867 |
| 4,696,688 | 9/1987 | Mehra | 62/17 |
| 4,740,222 | 4/1988 | Mehra | 62/17 |
| 4,743,282 | 5/1988 | Mehra | 62/17 |
| 4,832,718 | 5/1989 | Mehra | 62/17 |
| 4,883,514 | 11/1989 | Mehra | 62/17 |
| 4,883,515 | 11/1989 | Mehra et al. | 62/17 |
| 5,220,097 | 6/1993 | Lam et al. | 585/809 |
| 5,224,350 | 7/1993 | Mehra | 62/20 X |
| 5,326,929 | 7/1994 | Mehra et al. | 62/17 X |

OTHER PUBLICATIONS

Szatny et al., "Reporting Performance of a Field Test of The Mehra Process Nitrogen Rejection Unit," Gas Research Institute, Topical Report (Nov. 1993), Houston, Tex., pp. 1–17.

"Mehra vs. Cold–Box: The Final Chapter," Gas Processors Report (Sep. 6, 1993), Houston, Tex.

"Cold–Box Answers Back," Gas Processors Report (Jul. 12, 1993), Houston, Tex.

"Mehra Plant Beats Computer", Gas Processors Report (Jun. 14, 1993), Houston, Tex.

Mehra et al., "Noncryogenic $N_2$–rejection process gets Hugoton field test," Oil & Gas Journal (May 24, 1993), pp. 62–71.

Mehra et al., "Non–Cryogenic Absorption–Based Mehra Process Technology Upgrades Hugoton Gases," Advances in Nitrogen Rejection Tech. Sym., AIChE '93 Spring Nat'l Mtg. (Mar. 29, 1993), Houston, Tex., pp. 1–15.

Yuv R. Mehra, "Can We Really Afford to Keep Burning Light Olefins and Hydrogen in our Refineries?," CMAI Seminar, Houston, Tex. (Mar. 24–25, 1993), pp. 1–10.

"Nitrogen Rejection Made Easy," Gas Processors Report (Dec. 7, 1992), Houston, Tex.

(List continued on next page.)

*Primary Examiner*—Richard L. Chiesa
*Attorney, Agent, or Firm*—Arnold, White & Durkee

[57] ABSTRACT

An absorption process for separating a feed gas stream having components with a spectrum of volatilities including volatile (light) components, intermediate volatility components, and least volatile (heavy) components. The disclosed process includes the steps of: (1) contacting the feed gas stream with a liquid lean solvent stream in an absorber to produce a light product gas stream that is composed of predominantly light components and a rich solvent stream containing most of the intermediate and heavy components; (2) flashing the rich solvent stream at reduced pressure in a flash zone to produce an intermediate product gas stream composed predominantly of intermediate components and a lean solvent stream; (3) conveying the lean solvent stream from the flashing zone to the absorber, wherein the lean solvent is composed predominantly of heavy components taken from the feed; the process does not use an external lean solvent. The process is particularly useful for rejecting nitrogen from natural gas and for recovering hydrogen from refinery and petrochemical process off-gases.

14 Claims, 3 Drawing Sheets

OTHER PUBLICATIONS

Yuv R. Mehra, "Using Non–Cryogenic Absorption to Reject Nitrogen From Subquality Natural Gases," Gas Separation International (Apr. 22–24, 1991), Austin, Tex., pp. 1–13.

James J. L. Ma, "Comparison of the Mehra Process for Nitrogen Rejection to a Cryogenic Process for Nitrogen Rejection from Subquality Natural Gas," Topical Report (Mar. 1991).

Pruitt et al., "Wyoming's Shute Creek plant uses NRU . . . ," Oil & Gas Journal (Oct. 9, 1989) Technology, pp. 78–82.

Yuv R. Mehra, "Recover and Purify Hydrogen Economically," NPRA Annual Meeting (Mar. 29–31, 1987), San Antonio, Tex.

Yuv R. Mehra, "Mehra Process Flexibility Improves Gas Processing Margins," 66th Annual GPA Convention (Mar. 16–18, 1987), Denver, Colo.

Yuv R. Mehra, "Processing Hydrocarbon Gases with the Mehra Process Technology," Chemical Engineering (Oct. 27, 1986), Houston, Tex.

Fair et al., "Ethylene purification—demethanization," Chemical Eng. Progress, vol. 54, No. 12 (Dec. 1958), pp. 39–47.

ABSORPTION PROCESS WITHOUT EXTERNAL SOLVENT

FIELD OF THE INVENTION

This invention relates to physical absorption separation processes. The invention relates particularly to removing nitrogen from natural gas and to recovering hydrogen from refinery and petrochemical plant off-gas streams.

BACKGROUND OF THE INVENTION

Nitrogen Rejection from Natural Gas

Natural gas is a mixture of methane and light hydrocarbons (ethane, propane, butanes, pentanes, and small amounts of hexanes, heptanes and heavier components). Nitrogen is commonly found in natural gas. Other impurities in natural gas include helium, hydrogen sulfide, carbon dioxide, and water. Occasionally, cyclic and aromatic compounds occur in natural gas.

The composition of natural gas streams vary over a wide range as indicated by the data presented in Table 1. Nitrogen content in natural gas varies from a few percent to over 50%. The nitrogen may have formed naturally or have been introduced by injection into oil wells to stimulate production.

Gas pipeline transmission systems limit the allowable maximum content of non-combustible gases, nitrogen and carbon dioxide in natural gas because non-combustible gases lower heating value. The maximum specification for noncombustibles ranges typically between about 2 mol. % and about 8 mol. %. The Gas Research Institute estimates that there are about 55 trillion cubic feet of natural gas reserves in the continental United States that are "subquality". The Gas Research Institute defines natural gas containing more than 4 mole % nitrogen as sub-quality. These gas reserves must be processed to reject nitrogen and other non-combustibles to be acceptable to most pipelines. In addition, production of oil that is associated with high nitrogen gas is impeded because government regulations bar producers from burning the nitrogen-rich gas or venting the gas into the atmosphere.

Currently, the predominant technology for rejecting nitrogen from natural gas is cryogenic. The natural gas feed is liquefied by flashing the gas across Joule-Thompson valves or expanders to achieve very low temperatures (as low as −300° F.). Then, nitrogen is fractionated overhead out of the liquefied natural gas in a distillation tower forming a bottoms stream of methane with low nitrogen content. Cryogenic processes are intensively heat exchange integrated to reduce power consumption, e.g., incoming feed is cooled by heat exchange against outgoing cold product streams, thus conserving most of the energy that went into refrigerating the product.

Nitrogen rejection adds significantly to the cost of producing natural gas. Currently, most high nitrogen reserves are not produced because the margin between the cost of bringing the gas to the surface at the wellhead and the market price of gas at the pipeline is not sufficient to pay for rejection. Cryogenic processes have been thoroughly optimized and there is little prospect that the cost of cryogenic separations can be significantly reduced. Cryogenic processes are inherently expensive because of the very low temperatures encountered. Feeds must be purified to very low concentrations of water, carbon dioxide and mercury because minute amounts of these impurities have deleterious effects at cryogenic temperatures. Exotic, costly materials are required to withstand cryogenic temperatures. The intensive heat exchange integration required to reduce energy consumption makes cryogenic units difficult to control and operate and impossible to adapt to changing feeds and product slates, which are often required in energy markets. Clearly, there is opportunity for new cost effective and flexible rejection technology which will allow production of our vast high nitrogen natural gas resources.

Hydrogen Recovery from Refining and Petrochemical Off-gases

Demand for hydrogen to desulfurize feedstocks and liquefy heavy fractions in refining and petrochemical operations is increasing because sulfur in crude oils now being refined is increasing and more heavy crudes with higher carbon-to-hydrogen ratio are being produced. Most of the required chemical hydrogen is made on purpose by steam reforming or partial oxidation of methane and other hydrocarbons. It is estimated, however, that refining and petrochemical plants in North America are burning off-gases containing 1,500 to 2,000 million cubic feet per day of recoverable hydrogen. Several major off-gas sources of hydrogen are listed in Table 2. Apparently, even though the chemical value of hydrogen is two to three times its fuel value, it is cheaper to make on-purpose hydrogen than to recover hydrogen in these off-gas streams using current technology (cryogenic, membrane, and pressure swing adsorption processes). Clearly, there is opportunity for a new, flexible process which can make recovering hydrogen from off-gases cost competitive with on-purpose hydrogen.

Mehra Process[SM]

There is a need for new technology for rejecting nitrogen from natural gas that is cost effective and flexible and can make production of our high nitrogen natural gas reserves profitable. Also, there is need for new technology to recover hydrogen from refinery and petrochemical off-gas streams which are currently burned.

New processes have been developed for rejecting nitrogen from natural gas and recovering hydrogen from petrochemical off-gases which offer promise of opening these markets. They are described in U.S. Pat. Nos. 4,832,718 and 4,740,222, which are incorporated herein by reference. These processes use Mehra Process[SM] technology in which optimized absorption process technology is synergistically combined with certain selected solvents to minimize investment and operating costs. The Mehra processes operate at a higher temperature than cryogenic processes, so they have advantages over cryogenic processes: 1) they do not require exotic cryogenic construction materials; 2) feed purification specifications are more relaxed; 3) the processes are not as heat exchange integrated, so they are easier to operate; and 4) the processes adapt easily to changes. Process conditions can be changed quickly "on-line" with no adverse impact on operability and without equipment modifications to alter product stream compositions or maintain product composition should feed composition change.

BRIEF DESCRIPTION OF THE DRAWINGS

In the interest of clarity, pumps, heat exchangers, control valves, control systems, and auxiliary equipment items that are necessary for a practical and safe operating unit have intentionally been left out if not required to elucidate the inventive concept. These deletions are generally understood by those skilled in the art and do not limit the scope of the invention.

The three flowsheets are representative embodiments of the invention. Skilled process engineers will recognize that many other process designs can be devised that embody the present invention.

SUMMARY OF THE INVENTION

The present invention is an improved embodiment of the Mehra Processes which was first described in U.S. Pat. No. 4,832,718. Mehra Processes are absorption processes for separating a feed gas consisting of components with a spectrum of volatilities ranging from very volatile components such as non-condensible gases (hydrogen, nitrogen) to intermediate components such as methane, ethylene, and ethane to heavy components such as C2+ hydrocarbons. The Mehra processes can separate the feed into a light product stream consisting predominantly of the more volatile (light) component or components and another product stream consisting predominantly of less volatile (heavier) components. The Mehra process can separate the feed stream into three product streams: a light product stream consisting predominantly of light components, and intermediate product stream consisting predominantly of feed components with intermediate volatilities, and a heavy product stream consisting predominantly of heavy components. The volatility cut points between the product groups can be varied up or down among adjacent components by changing operating conditions, e.g., the least volatile component of the most volatile group can become the most volatile component of the intermediate group.

The separation of the light components from the feed is accomplished in an absorption column in which the feed gas flows up the column and is countercurrently contacted with an absorption solvent which flows down the column. Intermediate and heavy components are absorbed by the solvent and the rich solvent leaves the column as the bottoms stream. The light product stream is the overhead gas stream from the tower.

The present invention is distinguished by the combination of two features. One feature is that the solvent is regenerated by flashing the absorber bottoms stream to reduced pressure in one or more flash drums connected in series with no external heat added. The other feature is that the absorption solvent consists predominantly of heavy components supplied from the feed; except for the initial batch of solvent charged to start up the process, no external solvent is used and no external solvent is required to replenish solvent lost in product streams. Elimination of the external solvent reduces investment and operating costs. Solvent storage, pumping and metering facilities are not required. The costs and equipment associated with buying, receiving, storing and charging makeup solvent are eliminated. These are particularly significant advantages for gas treatment units located in remote sites.

Important aspects of the present invention are the techniques used for control of inventory of solvent in the process. The solvent inventory reservoir is maintained in the solvent regeneration flash drums. The product streams leaving the process contain small amounts of heavy components. If less heavy components come in with the feed to the absorber than leave in the light and intermediate products streams, the solvent inventory will decrease with time. If more heavy components come into the absorber in the feed than leave in the product streams, then the solvent inventory will increase with time. The techniques used to stabilize solvent inventory are based on the fact that the product streams leave the process saturated with heavy components. Accordingly, the concentration of heavy components in a product stream is a function of the temperature of the stream. Reducing a product stream temperature reduces the concentration of heavy components in that stream, and increasing the product stream temperature increases the heavy components in that stream. Therefore, solvent inventory can be stabilized by adjusting the temperatures of the product streams to make the heavy components coming into the absorber in the feed equal the heavy components leaving in the product streams.

Alternatively, if heavy components in the feed exceed heavy components in the products, solvent inventory will increase with operating time. Excess solvent inventory accumulated in the flash drums is removed to stabilize inventory. The solvent is comprised of primarily heavy components which can be sold as a product or can be blended into a product stream.

For the embodiments of this invention in which a heavy product stream is produced in addition to a light and an intermediate product stream, there are additional ways to manage inventory control. The heavy product stream is produced by cooling the feed stream to condense heavy components before the feed stream is conveyed into the absorber. The heavy product condensate is separated from the feed stream and the feed stream is conveyed to the absorber. Heavy components are diverted from the heavy product stream to the flash drums as required to maintain inventory. Alternatively, the temperature of the feed stream is controlled to hold the solvent inventory constant. The feed gas stream from which the heavy product condensate is separated is, of course, saturated with heavy components. Increasing the temperature of the feed stream increases the heavy components in the feed gas stream. Therefore, the temperature of the feed gas stream is adjusted to make the heavy components in the absorber feed equal the heavy components in the light and intermediate product streams for stabilizing solvent inventory.

Application to Natural Gas Nitrogen Rejection

An important commercial application of the present invention is rejection of nitrogen and helium from natural gas. In natural gas rejection applications, the natural gas (methane) product stream is the intermediate product stream. The nitrogen and other non-condensible gases are rejected in the light product stream. The natural gas is compressed and delivered into a natural gas transmission pipeline. Typically, the pipeline operators require that the concentration of nitrogen and other non-combustible gases in the natural gas be reduced to between 1 mole % and 10 mole %, more preferably between 2 mole % and 5 mole %, and most preferably between 2 mole % and 3 mole %. Usually, energy market conditions dictate that a heavy product stream consisting predominantly of ethane and heavier hydrocarbons be produced. The heavy product stream is produced by cooling the feed stream to condense heavy components. The heavy product stream is separated from the feed stream and the feed stream is conveyed to the absorber. The heavy stream is usually sold as an LPG fuel, or for chemical feed stock material.

An advantage of the process of the present invention is that absorption tower operates at natural gas feed line pressure which is typically in the range of 150 to 3000 psia. Accordingly, the rejected nitrogen stream is produced at pressures high enough that the stream can be re-injected into well formations to enhance recovery of oil and gas.

Helium contained in the natural gas feed appears in the light product (rejected nitrogen) stream. If helium is present in the light product stream in sufficient quantity to cost-effectively recover it, the light product stream is conveyed to a helium recovery unit before discarding it. Helium recovery in conjunction with Mehra processes is disclosed in U.S. Pat. No. 5,224,350, which is incorporated herein by reference.

Application to Hydrogen Recovery

Another important commercial application of the present invention is to recover hydrogen from refinery and petrochemical plant off-gas streams. In hydrogen recovery applications, hydrogen is recovered in the light product stream. If, as is commonly the case, the hydrogen feed stream contains methane, then the intermediate product stream produced is a methane-rich stream that is suitable for fuel gas. Usually, energy product market conditions dictate that a heavy product stream be produced from the feed gas. The heavy product stream is produced by cooling the feed stream to condense heavy components which include ethylene, ethane and heavier hydrocarbons. The heavy product stream is separated from the feed stream and the feed stream is conveyed to the absorber. The heavy product stream is sold as an LPG fuel or used as a chemical raw material. If it is not cost effective to produce a heavy product stream, then the heavy components in the feed leave the process in the intermediate product stream.

Non-condensible impurities including CO and nitrogen are commonly present in hydrogen off-gases. Noncondensibles appear in the light product stream along with the hydrogen. Many hydrogen applications require that noncondensible impurities be reduced to very low residual concentrations. For these applications, the light product stream coming overhead from the absorber is conveyed to a suitable hydrogen purification unit such as a pressure swing adsorption (PSA) system. These systems can produce hydrogen streams as pure as 99.995 mole %.

Hydrogen bearing off-gases from ammonia plants contain nitrogen. The nitrogen leaves the process in essentially the hydrogen-rich light product stream in the same ratio to hydrogen as in the feed. Typically, applications for this stream require that the hydrogen-to-nitrogen ratio be increased. This can be accomplished in any of the commercial hydrogen purification systems such as a PSA unit.

Experience with Mehra processes shows that, while technically feasible, it usually is not cost effective to reduce the hydrocarbon concentration of the hydrogen-rich light product stream to less than about 5 to 15 mole %. To make high purity hydrogen, rather than drive the Mehra absorber to non-optimal conditions, the better way is to operate the absorber in its optimal mode and to convey the hydrogen-rich light product stream from the absorber to a hydrogen purification unit to accomplish the final purification.

DETAILED DESCRIPTION OF THE PREFERRED EMBODIMENTS

Figure 1:
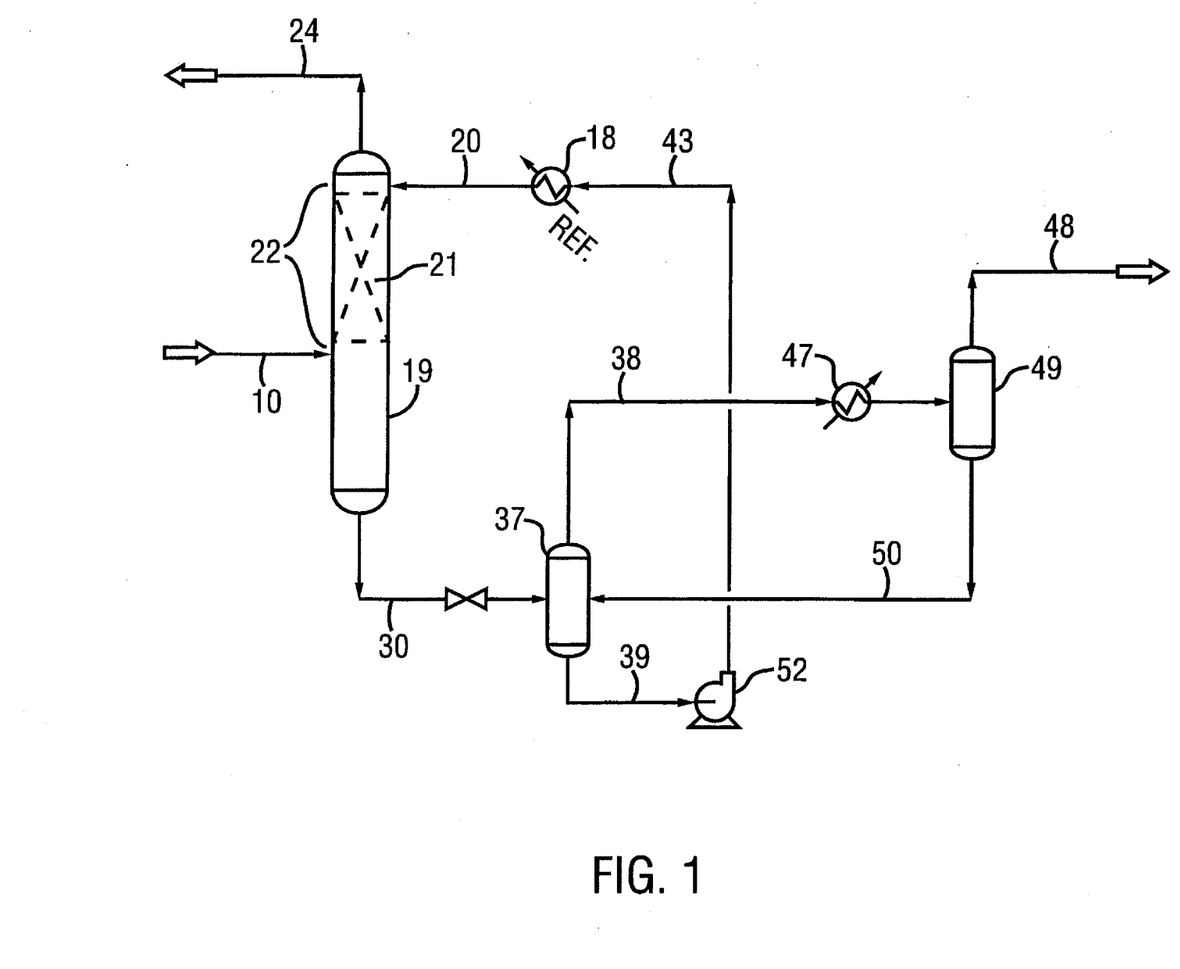
FIG. 1 is a flow diagram which illustrates the features of this invention in its simplest embodiment.

The flowsheet of FIG. 1 depicts the invention in its simplest embodiment in which the feed is separated into a light product consisting predominantly of light components and a heavy product consisting predominantly of heavy components. The feed gas 10 is introduced into the bottom of an absorber column 19 and flows up the column. Lean solvent is introduced near the top of the column and flows down the column countercurrently contacting the gas stream. The absorber is packed with Raschig rings or other packing 21 with large surface area and low pressure drop that is conducive to liquid/gas mass transfer. Alternatively, distillation trays such as sieve or valve trays can be used to affect the required mass transfer.

The solvent absorbs the intermediate and heavy components from the feed stream. The overhead gas stream leaving the top of the absorber 24 is the light product stream which consists predominantly of light components. The bottoms stream 30 is rich solvent which now contains the intermediate and heavy components absorbed out of the feed gas stream.

The solvent is regenerated by flashing to a lower pressure in one or more flash drums in series. (One flash drum 37 is shown in FIG. 1). The overhead stream from the flash drum, stream 38, consists of intermediate and heavy components from the feed. It is cooled in the product cooler 47 to partially condense the heavy components. The condensate is separated from the flash drum overhead stream in the product separator 49 and recycled back to the flash drum through line 50. The residual gas stream is the heavy product stream and it contains most of the intermediate and heavy components that came in with the feed.

The bottoms stream from the flash drum, stream 39, is the lean solvent stream which is pumped into the top of the absorber. It consists predominantly of heavy components derived from the feed. As indicated in FIG. 1, the lean solvent stream can be pumped through a solvent cooler 18 to reduce its temperature before it is conveyed into the top of the absorber 19. The lean solvent stream is comprised predominantly of heavy components supplied from the feed stream.

An inventory of solvent is maintained in the flash drum. The solvent inventory is stabilized by controlling the temperatures at the outlet of the solvent cooler and the product cooler to make the heavy components coming into the absorber in the feed equal to the heavy components leaving in the product streams. The heavy product stream is saturated with heavy components so increasing its temperature increases heavy components in the stream and reducing the temperature reduces heavy components in the stream. The light product stream leaving the top of the absorber, stream 24, is also saturated with heavy components. Reducing the temperature of the solvent going into the absorber 20 reduces the temperature at the top of the absorber which, in turn, reduces the partial pressure of heavy components in the light product stream.

The process is distinguished by two features:

1) The solvent is regenerated by flashing the absorber bottoms stream to reduced pressure with no heat added to the flashing stream.

2) The solvent consists predominantly of heavy components supplied from the feed. No external solvent is required.

Figure 2:
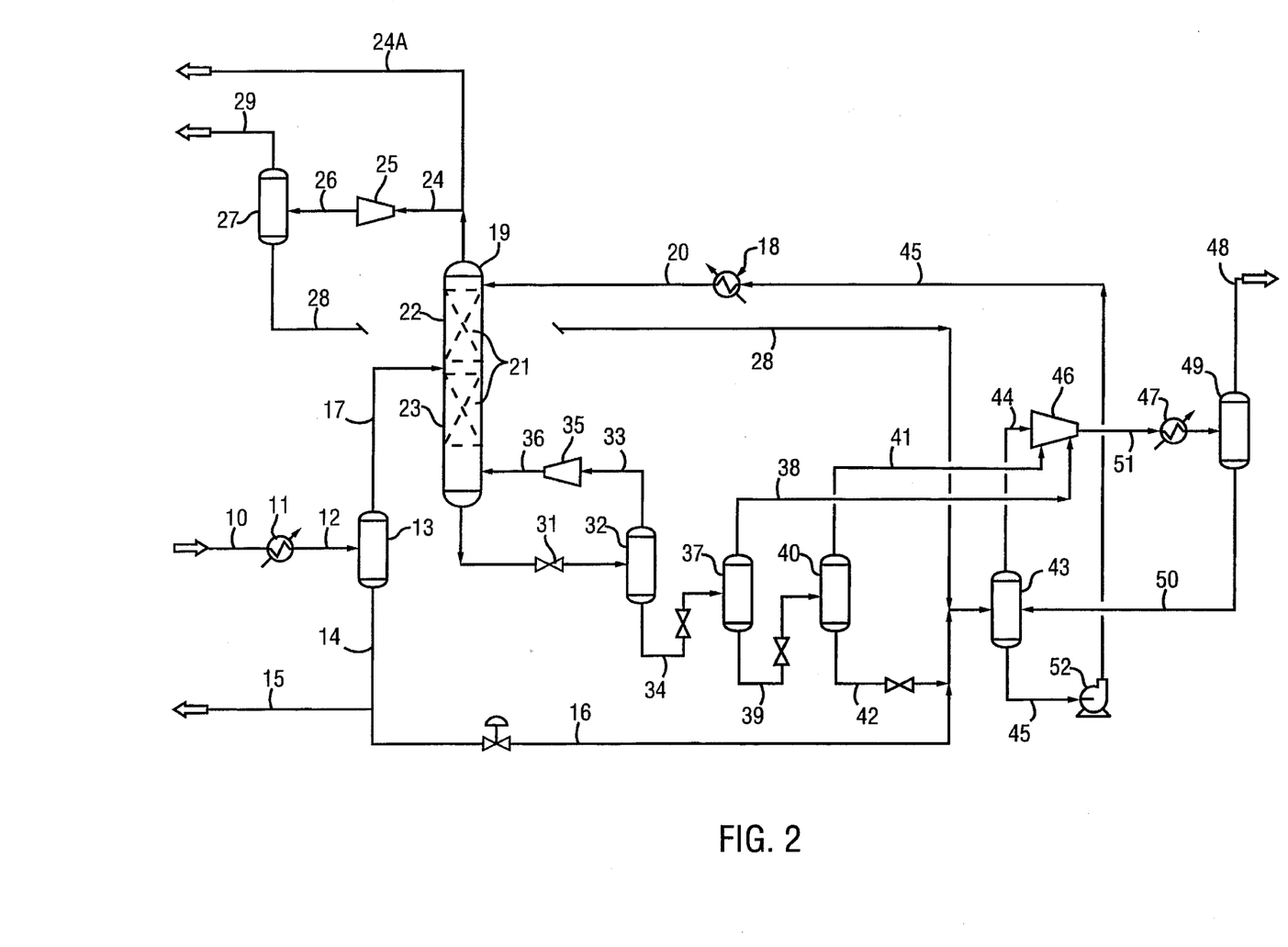
FIG. 2 is a flow diagram which illustrates the invention in a preferred embodiment.

FIG. 2 is a flow plan showing the present invention in a preferred embodiment in which three product streams are produced: a light product stream consisting predominantly of light components; an intermediate product stream consisting primarily of intermediate components; and a heavy product stream consisting predominantly of heavy components is produced.

Prior to entering the process, the feed stream is dried to a water dewpoint to preclude formation of solid hydrates in the process. The water dewpoint specification is typically in the range of about −30° F. to about −150° F.; the lower the minimum temperature in the process, the lower the dewpoint specification. These dewpoints can be readily achieved with conventional drying technology such as a molecular sieve or glycol injection drying system.

The feed stream 10 is cooled in feed cooler 11 to condense the heavy product stream which consists of predominantly heavy components. The heavy product condensate stream 14 is separated from the cooled feed gas stream 12 in the feed separator drum 13 and removed as the heavy product separator bottoms stream 15.

The overhead stream from the feed separator 17 is conveyed into the absorber stripper 19. Lean solvent which has been cooled in the solvent cooler 18 is conveyed into the top of the absorber stripper through line 20.

The absorber stripper 19 contains packing 21 which promotes liquid/gas mass transfer exchange, such as Raschig rings or saddle packing. Alternatively, distillation trays such as bubble caps, sieve trays, or high efficiency trays with multi downcomers can be used to affect liquid gas mass transfer exchange in the tower.

The section of the absorber stripper above the feed point is the absorption section 22. In the absorption section 22, the rising feed gas stream countercurrently contacts the falling solvent stream. Intermediate and heavy components are absorbed out of the feed gas stream into the solvent stream. The absorber stripper overhead stream 24 contains most of the light components which were in the feed stream 10.

It is usually important to minimize intermediate and heavy components in the absorber stripper overhead gas stream. Measures which improve absorption of intermediate and heavy components include, in the design phase, providing more mass transfer stages-more mass transfer surface area and higher efficiency-in the absorption section. Operating measures include increasing lean solvent circulation rate relative to gas feed rate, and reducing the temperature of the lean solvent stream coming into the tower. Obviously, these measures raise costs, so there is an economic trade-off between minimizing overhead losses and optimizing cost.

The absorber stripper 19 operates at feed line pressure, typically 150 to 3000 psi. In some applications, the light product exits the process at absorber stripper pressure through stream 24A. In other applications, the light product stream is vented to the atmosphere via line 24. The stream pressure can be reduced across a control valve, or, as shown in FIG. 2, through an expander 25 to recover shaft power from the expanding gas. The temperature of the absorber stripper overhead gas stream 26 drops sharply as its pressure is reduced. Temperature drops more through an expander than a control valve because, through an expander, the expansion is isentropic with work extracted from the expanding gas, whereas, across a valve, the expansion is adiabatic. In either case, the temperature reduction provides one last opportunity to recover some of the heavy and intermediate components in the light product since intermediate and heavy components condense as the gas stream temperature declines during the pressure reduction. An expander induces lower exhaust temperatures and, hence, more condensation than the letdown valve because the gas expands isentropically in the expander, but adiabatically in the letdown valve.

The condensate liquid is separated from the light product 29 in the light product separator 27 via stream 28, and is recycled back into the process at a downstream point.

An energy saving feature which is usually cost effective (not shown in FIG. 1) is to cool the feed coming into the process by heat exchange against the cold light product stream leaving the process to conserve refrigeration energy.

This embodiment of the invention includes a stripping section 23 in the absorber 19 below the feed point. Solvent rich in intermediate components flows down from the absorption section into and down through the stripping section. The function of the stripping section 23 is to remove light components from the solvent while retaining intermediate components in the solvent. This is accomplished by countercurrently contacting the rich solvent as it cascades down the stripping section with a stripping gas stream moving up the column. The stripping gas stream is formed by flashing the absorber stripper bottoms stream 30 from tower pressure to a lower pressure across valve 31 into first absorber stripper bottoms flash drum 34. The stripping gas stream is taken overhead from the first flash drum 33, compressed to tower pressure using a suitable compressor 35, such as a reciprocating or centrifugal compressor, and conveyed into the absorber stripper tower near its bottom as stream 36.

Optionally, a heat exchanger (not included in FIG. 2) can be installed at the outlet of the stripping gas compressor, line 36, to adjust the temperature of the stripping gas going into the bottom of the absorber stripper. The heat exchanger provides another degree of control over stripping effectiveness in the bottom of the absorber stripper 19.

In some applications, the concentration of light components in the intermediate products stream must be limited to meet intermediate product specifications. Light components remaining in the bottoms stream from the first flash drum, stream 34, leave the process in the intermediate product stream. Therefore, the ratio of light components to intermediate components in the first flash drum bottoms stream must be controlled to keep the concentration of light components in the intermediate product below the maximum light components specification. The principal means for controlling the ratio of light components to intermediate components in the first stage flash drum bottoms stream 34 is by adjusting the pumping rate of the stripping gas compressor. Increasing flow of stripping gas to the absorber stripper reduces light components in the first stage flash drum bottoms stream 34. (Increasing stripping gas compressor pumping rate reduces pressure in the first flash drum 32 which increases the overhead gas flashed out of the absorber stripper bottoms stream in the first flash 32.) If a stripping gas heat exchanger is included in the process, another means to control the ratio of light components to intermediate components in the first flash stage bottoms stream is to control the temperature of the stripping gas going into the bottom of the absorber stripper using a heat exchanger; increasing temperature of the stripping gas reduces the ratio of light components to intermediate components in the first flash drum bottoms stream by increasing temperature in the bottom of the absorber stripper, stream 30.

The rich solvent is regenerated by separating the intermediate product from the rich solvent by subjecting the bottoms stream from the first flash drum 34 to one or more flashing stages in series, during which the rich solvent is cascaded to successively lower pressure across flash valves. Hydraulic turbines may alternatively be employed in lieu of pressure letdown valves. The number of flash stages that are optimal depends on feed and products specifications and the cost of adding and operating additional flash drums. The process of FIG. 1 employs three flashing stages-the second flash drum 37, the third flash drum 40, and the fourth flash drum 43. The overhead gas streams from the second, third and fourth flash drums 38, 41 and 44, which contain the intermediate components, are compressed in the intermediate product compressor 46 to pipeline or storage pressure. The intermediate product compressor 46 can be either a reciprocating or centrifugal compressor.

It is usually advantageous to use a multi-stage intermediate product compressor. Overhead gas from the second (upstream) flashdrum 37, which is at the highest pressure, is fed into the suction of the high pressure (downstream) compressor stage 38; overhead gas from the fourth (downstream) stage 43, which is at the lowest pressure, is fed into the suction of the low pressure (upstream) compressor stage 44; overhead from intermediate flash stages 40 are fed into intermediate compressor stages 41. Use of multiple flash drums at decreasing pressures, arranged as in FIG. 1, reduces the size and power consumption of the intermediate product gas compressor 46 relative to using only one flash drum and feeding all the overhead flash gas into the suction of the low pressure upstream stage suction of the compressor, since not all the flash gas has to be compressed up from the lowest downstream flash drum pressure.

The compressor discharge stream 51 is cooled in the intermediate product cooler 47 to condense heavy components. The condensate is separated in the intermediate product separator 49 and collected as the bottoms stream 50. The overhead stream 48 from the intermediate product separator 49 is the intermediate product stream.

The bottoms stream 45 from the fourth (most downstream and lowest pressure) flash drum 43 is the lean solvent stream. It consists predominantly of heavy components derived from the feed stream 10. The lean solvent stream is pumped from the fourth flash drum through the solvent cooler 18 to a specified reduced temperature and into the top of the absorber stripper tower stream 20.

Unavoidably, some heavy feed components leave the process in the intermediate product stream 48. Losses of heavy components in the intermediate product stream can be reduced by lowering the temperature at the outlet of the intermediate product cooler 47 which increases condensation of heavy components out of the intermediate product stream. Also unavoidably, heavy and intermediate components leave the process in the light product stream 24 or 24A. These losses can be reduced by lowering the temperature of the lean solvent at the outlet of the solvent cooler 18, which reduces the temperature at the top of the absorber stripper 19, which, in turn, reduces the vapor pressure of intermediate and heavy components at the top of the absorber stripper in the light product gas stream 24 or 24A.

Commonly, a low temperature refrigerant such as boiling freon, propylene or propane is specified as the cooling medium in the intermediate product cooler 47, the solvent cooler 18, and the feed cooler 11 to attain cold exchanger outlet temperatures to reduce heavy component losses.

Loss of heavy components from the process is mitigated by recycling the bottoms stream 28 from the light product separator 27, which contains heavy and intermediate components, and the bottoms stream 50 from the intermediate product separator 49, which contain heavy components, into a flash drum (in FIG. 2 the fourth flash drum 43). However, if more heavy components leave in the product streams than come into the absorber stripper via stream 17, over time, solvent (heavy component) inventory in the flash drums will be depleted. Accordingly, total inventory of liquid in the flash drums is monitored. If liquid inventory in the flash drums falls below the minimum setpoint, solvent must be replenished. One way to make up solvent is to divert some of the heavy product stream 15 to a flash drum (in FIG. 2 to the fourth flash drum 43 through line 16).

Alternatively, heavy components coming into the absorber stripper 17 can be increased by increasing the temperature of the outlet of the feed cooler 11 so that less heavy components are condensed out of the feed stream 10 to replenish and stabilize solvent inventory.

Another alternative is to reduce the temperature at the outlet of the intermediate product cooler 47 and the solvent cooler 18 to reduce solvent losses from the process in streams 48 and 24 or 24A, respectively.

It is also possible that more heavy components come into the process in the feed than leave in the product streams. In this case, solvent inventory in the flash drums will increase with time and exceed the maximum setpoint. To correct for solvent accumulation, the actions discussed above to avoid depleting solvent are reversed.

Finally, it is possible, by adjusting outlet temperatures from the intermediate product cooler 47, the feed cooler 11, and the solvent cooler 18, to make the heavy components leaving the process equal the rate the heavy components coming into the absorber stripper, via stream 17, which will stabilize solvent inventory.

Figure 3:
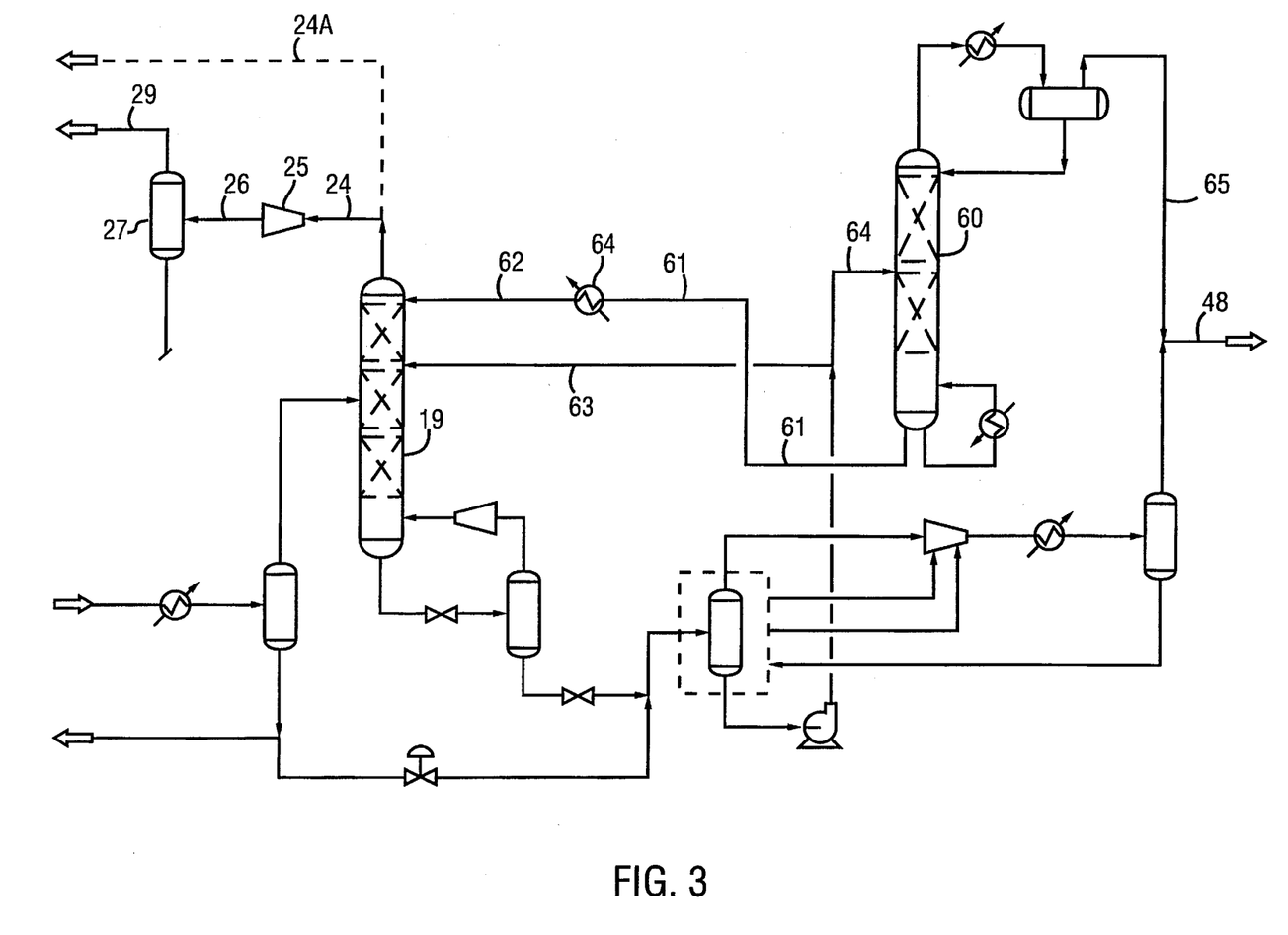
FIG. 3 is a flow diagram which illustrates the invention in a more complex but alternative preferred embodiment.

The process of FIG. 3 is more complex than the process of FIG. 2, but it is also a preferred embodiment of the present invention. FIG. 3 contains one more tower, the solvent fractionator 60, than FIG. 2, and utilizes two lean solvent streams, a main lean solvent stream 63 and a slip lean solvent stream 62. The lean solvent slip stream 62 contains less intermediate components than the lean solvent stream of FIG. 1, and it is conveyed into the absorber stripper at the top of the tower via line 62. The main solvent stream 63 has about the same composition as the lean solvent stream in FIG. 2, and it is conveyed into the absorber stripper 19 via line 63 at a point below line 62.

The solvent fractionator 60 produces the lean solvent slip stream 61 as the fractionator bottoms stream by fractionating part of the bottoms stream 64 from the final downstream flash drum. The lean solvent slip stream 61 flow rate is typically about 15% to 70% of the main solvent stream flow rate. The lean solvent slip stream 61 is pumped (pump not shown on FIG. 3) through the solvent cooler 64, where its temperature is reduced, and into the top of the absorber stripper 19, where it contacts the absorber stripper overhead stream as it exits the tower.

The overhead stream from the solvent fractionator 65 consists predominantly of intermediate components and is added to the intermediate product stream 48.

The advantage of the process of FIG. 3 over the process of FIG. 2 is that concentration of intermediate and heavy components in the light product stream 24 or 24A with the process of FIG. 3 can be significantly lower than can be achieved with the process of FIG. 2. Since the overhead gas stream 24 or 24A leaving the stripper absorber is in equilibrium with the lean solvent slip stream, and since the slip stream solvent contains less intermediate components than the main lean solvent stream, the absorber stripper overhead stream contains a lower concentration of intermediate components. So, FIG. 3 is the preferred process if achieving low concentrations of intermediate and heavy components in the light product stream is important.

Note that in both the processes of FIG. 2 and 3, solvent is regenerated by flashing the rich solvent stream 30 from the absorber stripper 19 to lower pressure, and the absorption solvent streams 45, 62 and 63 consist predominantly of heavy components supplied from the feed; no external absorption solvent is used and no external solvent makeup is required. The solvent composition will change when feed composition is changed because solvent composition is influenced by the relative concentration of the heavy components in the feed and their volatility. Also, solvent composition changes when process operating conditions are changed, particularly temperatures. It has been observed that changes in the composition of the solvent do not affect efficiency or operability of the process.

When initially starting up the process of this invention, there is of course no solvent inventory in the flash drums. The required solvent inventory can be accumulated by operating the unit with no lean solvent flow to the absorber stripper until liquid level in the flash drums reaches the set points. The composition of the solvent in the flash drums will, over a period of a few hours, equilibrate to its steady state composition. Alternatively, heavy product condensed out of the feed, stream 16, can be totally diverted to the flash drums until the solvent levels reach the setpoint. This batch of solvent can be a mixture of components blended to have a composition similar to the composition of the heavy components, or heavy component condensate obtained from the feed for the plants or it can be one of the heavy components. Whatever the initial solvent composition, the composition will, over a period of several hours of operation, equilibrate to a steady state composition consisting primarily of heavy components in the feed, as determined by the operating conditions in the unit, and no external solvent will be required to replenish solvent losses. Another startup method is to fill the flash drums with an initial charge of solvent made up of one or more of the heavy components in the feed. The solvent composition in the flash drums will equilibrate quickly to its steady state composition comprising heavy components derived from the feed.

DISCUSSION OF BACKGROUND INFORMATION

U.S. Pat. No. 3,633,371 discloses a process for recovering ethane and higher hydrocarbons from natural gas by cooling the natural gas stream to between −70° F. and −120° F. to partially condense the ethane and heavier components and separate the condensate from the natural gas. The cooled natural gas stream is then countercurrently contacted with an absorbent fluid, also between −70° F. and −120° F., to absorb the ethane and heavier components out of the natural gas stream. The absorbent consists essentially of saturated hydrocarbons having from 4 to 8 carbon atoms per molecule, and is preferably a hexane such as normal hexane.

U.S. Pat. No. 4,035,167 discusses absorption processes for separating ethane and ethylene from methane using an external absorption solvent. Rich solvent is regenerated by release of pressure or heating. Preferred solvents are cyclohexane, 1-chlorobutane and 1,1,1,-trichloroethane. Other external solvents disclosed in cited references include aromatic distillate, saturated hydrocarbons containing 4 to 8 carbon atoms, and unspecified "hydrocarbon oil".

An article entitled "Ethylene purification-demethanization," by J. R. Fair, W. L. Bolles, and W. R. Nisbet Inc. Chemical Engineering Progress (Vol. 54, No 2, December 1958), discusses absorption processes for separating ethylene and heavier components from methane. The process includes a fractionating absorber tower followed by a solvent regenerator fractionator. Solvents mentioned include aromatic distillate of 75–85 molecular weight, a propane-propylene fraction, and normal hexane.

U.S. Pat. No. 4,832,718 discloses processes for rejecting nitrogen from natural gas and for recovering hydrogen and methane rich fuel gas from refinery off-gas streams. The key teaching of the patent is use of external absorption solvents which meet certain selection criteria specified in the patent. The selection criteria ranges are molecular weight and UOP characterization factors which are different for paraffinic solvents, naphthenic solvents, and lighter aromatic solvents. All physical solvents from the group of paraffinic and naphthenic solvents must have molecular weights ranging from 75 to 140, plus benzene and toluene among the aromatic group. The group of paraffinic solvents is additionally defined as solvents having UOP characterization factors ranging from 12.0 to 13.5. The naphthenic solvents are defined as those having UOP characterization factors ranging from 10.5 to 12.0. Column 8, lines 42 to 53.

U.S. Pat. No. 4,883,514 discusses absorption processes for rejecting nitrogen from natural gas which use external lean oils as the absorption solvent. Solvents cited include N-methyl pyrollidone, dimethyl formamide, typical paraffinic lean oils, dimethylether of polyethylene glycol, and aromatic lean oils such as mesitylene. The patent teaches:

suitable lean oils include paraffinic, aromatic, and cyclo hydrocarbons and mixtures thereof in any proportion and having an average molecular weight of 75 to 250. Suitable aromatic compounds having methyl, ethyl or propyl aliphatic groups and specifically constituting a sub-group consisting of mesitylene, m-xylene, p-xylene and mixtures thereof, and aromatic streams rich in mixed xylenes, C9 alkylaromatics, and other C8–C10 aromatics, rich being defined with respect to the solvent as more than 15% by weight of the aromatic compound. (Column 6, lines 58 to 69.)

U.S. Pat. Nos. 4,526,594 and 4,623,371 disclose extraction processes for selectively removing C2+, C3+, C4+ or C5+ hydrocarbon components from a natural gas stream by contact with a physical solvent.

The physical solvent is selected from the group consisting of alkyl ethers of polyalkylene glycol, N-methyl pyrrolidone, dimethyl formamide, propylene carbonate, sulfolane, and glycol triacetate. The solvent is preferably selected from the group consisting of dimethyl ether or polyethylene glycol, dimethyl ether of polypropylene glycol, dimethyl ether of terramethylene glycol, and mixtures thereof, and the solvent most preferred is dimethylether of polyethylene glycol containing 3–10 ethylene units and having a molecular weight of 146 to 476." (Column 8, lines 54 to 64.)

U.S. Pat. No. 4,421,535 discloses an absorption process for removing ethane plus heavier hydrocarbon components from a sweet natural gas stream by contact with an alkyl ether of polyethylene or polypropylene glycol, or mixtures thereof.

U.S. Pat. Nos. 4,695,672 and 4,692,179 disclose processes for recovering C2+ to C5+ hydrocarbons from a hydrocarbon gas stream using a suitable preferential physical solvent that is rich in C8–C10 aromatic compounds having methyl, ethyl or propyl aliphatic groups, including mesitylene, n-propyl benzene, n-butyl benzene, o-xylene, m-xylene, p-xylene, and mixtures thereof.

U.S. Pat. No. 4,617,038 discloses an absorption process for recovering ethane and higher hydrocarbons from a hydrocarbon stream using a preferred physical absorption solvent defined as having a minimum relative volatility of methane over ethane of at least 5.0 and a solubility of at least 0.25 standard cubic feet of gaseous hydrocarbons per gallon of the solvent, or, alternatively, a preferential factor of at least 1.25. The rich solvent is regenerated to lean solvent via an intermediate flashing stage followed by distilling heavy components overhead in a fractionator column.

U.S. Pat. No. 4,578,094 discloses an absorption process for treating natural gas containing C5+ hydrocarbons. The solvent used is not specified.

U.S. Pat. No. 4,740,222 discloses the process flow sheets of FIG. 1 and 2 applied to recovering hydrogen from streams comprising hydrogen and hydrocarbons using an external absorption solvent:

A. Selected from the group consisting of dialyl ethers of polyalkylene glycol, N-methyl pyrrolidone, dimethylformamide, propylene carbonate, sulfolane, glycol triacetate, and C8 to C10 aromatic compounds having methyl, ethyl, propyl, or butyl aliphatic groups specifically constituting a sub-group or mesitylene, n-propyl benzene, n-butyl benzene, cumene, o-xylene, m-xylene, p-xylene, and mixtures thereof, and aromatic streams rich in mixed xylene, and other C8–C10 aromatics; and B. Selected for methane and heavier hydrocarbon components of said inlet gas stream such that:

(1) the relative volatility of hydrogen over methane is at least 4.5, and the hydrocarbon loading capacity, defined as solubility of methane in said solvent, is at least 1.0 standard cubic feet of methane to a gallon of said solvent, or (2) the preferential factor, determined by the multiplication of relative volatility of hydrogen over methane by the solubility of methane in solvent, in standard cubic feet of methane per gallon of solvent stream, are at least 4.5 . . . (Column 12, lines 61 to 68, and Column 13, lines 1 to 15.)

In a report entitled "Comparison of the Mehra Process for Nitrogen Rejection to a Cryogenic Process for Nitrogen Rejection from Subquality Natural Gas," published March 1991, by the Gas Research Institute in Chicago (GRI-90/0290; U.S. Dept. of Commerce National Technical Information Service PB91-222067), the authors compared the absorption process for rejecting nitrogen from natural gas of FIG. 1 with cryogenic processes. The paper does not discuss or specify the absorption solvent. The same information in less detail is covered in a paper entitled "Using Non-Cryogenic Absorption To Reject Nitrogen From Subquality Natural Gases," by Yuv R. Mehra and Dennis Leppin, presented at the Gas Separation International sponsored by the Center for Energy Studies, University of Texas at Austin, Texas during Apr. 22–24, 1991.

A paper read at the 1987 National Petroleum Refiners Association Annual Meeting on March 29–31 in San Antonio, Tex., entitled "Recover and Purify Hydrogen Economically," by Yuv R. Mehra, discussed the process of the present invention as applied to hydrogen recovery. The paper taught use of an external absorption solvent and make up of solvent losses with the external solvent.

European Patent EP-A 0211447 discloses absorption processes for scrubbing light hydrocarbons, particularly C2+ and C3+ hydrocarbons from gaseous mixtures. The patent teaches that preferred solvents have one or two rings formed by 5 or 6 carbon atoms, and the rings may be saturated, unsaturated, or partially saturated and, in total, contain between 9 and 17 carbon atoms.

In the May 24, 1993 issue of the Oil & Gas Journal, the inventors of the present invention published an article entitled "Noncryogenic N2-rejection process gets Hugoton field test." The article is a summary of a paper presented on Mar. 29, 1993 at the AICHE National Meeting in Houston. The paper and article described a field testing at Hugoton, KS of a commercial scale unit using a process similar to the process of FIG. 1 herein to reject nitrogen from natural gas. Neither the AICHE paper nor the Oil & Gas Journal article discussed the nature of the absorption solvent. At the time the paper and article were written, the inventors intended to use an external absorption solvent, hexane, in the Hugoton field test, although this was not disclosed at the AICHE meeting or in the article. The test unit was started up on Mar. 20, 1993 and the test was concluded on Aug. 19, 1993.

During the field test, the inventors conceived the present invention: to use heavy components in the feed as the solvent and not use external solvent to replenish solvent losses. Other than the initial solvent charge, no external solvent was used for the entire demonstration period. Both methods of stabilizing solvent inventory in the flash drums were demonstrated: replenishing solvent inventory with heavy product, and adjusting temperatures at the outlet of the feed cooler, product cooler and solvent cooler to make heavy component losses in the light and intermediate product streams equal heavy components in the feed to the absorber stripper. Hence, the process of the present invention was successfully reduced to practice during the Hugoton field test.

No product was sold during the test; the natural gas product stream was recycled back to the source.

A performance test of the Hugoton plant was sponsored by the Gas Research Institute. The results were published in a report by M. Szatny and G. Wood entitled "Test Performance Evaluation of Mehra Process of Nitrogen Rejection from Natural Gas," GRI Report, 93/0448, Feb. 1994. Even in this report, no solvent has been disclosed. Example One: Nitrogen Rejection from Natural Gas Table 3 is a material balance which shows how the process of FIG. 2 is applied to reject nitrogen from natural gas in the best mode contemplated by the inventors. (The stream numbers in Table 3 refer to FIG. 2).

The feed rate is 40 MMSCFD of natural gas containing 30 mol % nitrogen and 11 mol % C2+ hydrocarbons. The feed also contains small amounts of helium and carbon dioxide. The unit reduces nitrogen content of the natural gas product to 2 mol % while limiting methane losses in the rejected nitrogen to only 2% of incoming methane.

The light products stream 29 contains the rejected nitrogen and also the helium present in the feed. The intermediate product stream 48 is the natural gas product stream, suitable for transmission in the natural gas pipeline grid. The heavy product stream 15 is predominantly C2 to C6 hydrocarbons which can be sold as LPG fuel or for chemical raw material, or be blended into the natural gas product stream 48.

The feed stream 10 is dehydrated to a water dewpoint of $-150°$ F. in a mole sieve dryer unit before coming into the rejection plant. The dry feed 10 enters the nitrogen rejection unit at 80° F. and about 700 psig.

The feed stream is cooled to $-14°$ F. in feed cooler 11 by heat exchange with product streams which exit the process at very cold temperatures. (Feed/product heat exchange is not indicated on FIG. 1, but is the preferred mode for this application since it cost effectively reduces energy consumption for refrigeration). C2+ hydrocarbons condense out of the feed as it is cooled in feed cooler 11. The condensate is the heavy product 15. It is separated from the feed stream in feed cooler separator 13 as the feed cooler separator bottoms stream 14.

The cooled feed stream 17 is conveyed into the absorber stripper 19 at a point near the bottom of the absorption section 22 and flows upward countercurrently contacting the solvent stream 20. The absorber stripper operates at feed line pressure, 700 psia.

The solvent stream 20 enters into the absorber stripper at the top of the tower. It is the bottoms stream from the fourth flash drum 45 which has been cooled in solvent cooler 18, and it consists predominantly of C2+ components, which are the heavy components of the feed.

The rejected nitrogen and helium is contained in absorber stripper overhead stream 24.

In this application, the rejected nitrogen light product stream 24 is vented to the atmosphere. Rather than reducing pressure of the absorber stripper overhead stream 24 across a control valve, it is cost effective to reduce the pressure, from 700 psia to 43 psia, in the light product expander 25 and extract shaft power. The temperature of the gas stream falls to $-215°$ F. as it isentropically depressurizes in the expander so that the intermediate component, methane, and heavy components, C2+ hydrocarbons partially condense. The condensate is separated from the nitrogen stream in the light product separator as the bottoms stream 28 and recycled back into the process downstream. The cold rejected nitrogen stream 29 coming overhead from the light product separator, which is at $-215°$ F., is cross heat exchanged with incoming feed in feed pre-coolers (not shown on FIG. 1), and is vented to the atmosphere at $74°$ F.

In other applications, rather than venting the rejected nitrogen stream to the atmosphere, it is conveyed back down into a subterranean oil or gas formation to enhance production. Clearly, at locations where nitrogen injection enhancement is advantageous, one advantage of the Mehra nitrogen rejection process over cryogenic processes is that the rejected nitrogen stream is produced at high pressure suitable for injection without compression.

The C2+ solvent stream from the bottom of the absorption section 22 of the absorber stripper, enriched with absorbed methane, flows down through the stripping section 23 of the absorber stripper where it is countercurrently contacted with stripping gas 36. The function of the stripping section is to strip nitrogen and other light components out of the solvent stream. Since nitrogen in the absorber stripper bottoms eventually exits the process in the natural gas product stream, the molar ratio of nitrogen to methane in the absorber stripper bottoms must be reduced below the maximum concentration of nitrogen and other non-combustibles allowed by the gas pipeline system that will transport the gas. In this example, the molar ratio of nitrogen to methane in the bottoms stream 34 from the first flash drum is reduced to about 2%, which will make the mole % of nitrogen in the natural gas intermediate product 48 less than 2%.

The stripping gas stream is produced by flashing the absorber stripper bottoms stream 20 to a pressure of 360 psia in the first flash drum 32. The overhead stream from the first flash drum 32, which is the stripping gas stream, is compressed up to stripper absorber pressure of 700 psia using stripping gas compressor 33, then passed through a heat exchanger (not shown on FIG. 1), which adjusts the stream temperature to $94°$ F., and into the bottom of the absorber stripper. The stripping gas flow rate is 2420 lb/mol per hour.

In this example, three stages of flashing are used to regenerate the rich solvent and recover the natural gas: flash drums 37, 40, and 43, arranged in series. Three flash stages is the economic optimum for this application. For other applications, fewer or more stages may be optimal. The flash drums operate at successively lower pressures, 245 psia in the flash drum 37, 70 psia in the flash drum 40, and 20 psia in flash drum 43, respectively. The flash drum overhead streams 38, 41, and 44 contain the natural gas. They are compressed to natural gas pipeline pressure, 815 psia, in a four-stage reciprocating compressor 46. The upstream low pressure compressor stage takes suction from downstream flash drum overhead stream 44, the downstream high pressure compressor stage takes suction from the upstream flash drum overhead stream 38, and the intermediate compressor stage takes suction from the middle flash drum overhead stream 41. The fourth compressor stage takes suction from the discharge of the third stage and boosts the discharge pressure to pipeline pressure.

The compressed natural gas stream is cooled in the intermediate product cooler 47 to about $-9°$ F. using propane refrigerant coolant. Heavy, C2+, components condense in the intermediate product cooler 47. The condensate is separated from the natural gas in the intermediate product separator drum 49 and conveyed from the separator to the downstream flash drum 40 using line 50.

The bottoms stream 45 from the fourth stage flash, which consists predominantly of heavy, C2+, components derived from the feed, is the lean solvent stream. The stream is pumped through the solvent cooler 18, where it is cooled to $-25°$ F. (using propane refrigerant as the cooling medium), and then enters into the absorber stripper 19 at a point near its top via line 20.

The bottoms streams from the light product separator 27 and the intermediate product separator, which contain heavy, C2+, components, are conveyed to the fourth flash drum to reduce depletion of solvent inventory in the flash drums. The solvent inventory in the four flash drums is continually monitored. In this example, solvent inventory in the flash drums is stabilized by controlling the temperatures at the exit of the feed cooler 11, the solvent cooler 18, and the intermediate product cooler 47, to make heavy components going into the absorber stripper via stream 17 equal the heavy components leaving the process in the nitrogen rich light product stream 29 and the methane rich intermediate product stream 48. Solvent make-up to replenish the inventory is not required.

If the C2+ components lost in the rejected nitrogen and natural gas product streams were to exceed the C2+ components coming into the process in the feed to the absorber stripper 19, solvent would be continuously depleted. To replenish solvent inventory, heavy product from the feed separator 13 could be diverted to one of the flash drums via line 16 to replenish the solvent inventory. Alternatively, to equilibrate heavy component losses in the light and intermediate product streams to heavy components in the feed to the absorber stripper tower, one could raise the temperature at the exit of the feed cooler 11 which would bring more heavy components into the absorber stripper 19 or reduce the temperature at the exit of the intermediate product cooler 47, which would reduce the loss of heavy components in the natural gas intermediate product stream, or reduce the temperature at the exit of the solvent cooler 18, which would reduce the loss of heavy components in the nitrogen rich light product stream, or any combination of these temperature adjustments to replenish and stabilize solvent inventory.

As an energy saving option which is sometimes cost effective, the flash valves in lines 30, 34, 39 and 42 are replaced with hydraulic turbines which extract shaft work out of the expanding flashing streams which is converted to power. In addition, lower flash temperatures are achieved using turbines instead of valves which reduces the requirement for external refrigerants in the refrigerated heat exchangers used in the process.

Example Two

An overall material balance indicating how the process of FIG. 2 may be applied to recover hydrogen from a typical petroleum refinery offgas stream is presented in Table 4. (The stream numbers in Table 4 refer to FIG. 2).

The feed stream 10 contains 20 mole % hydrogen. (It is currently being burned as fuel gas.) The process of this invention recovers a light product stream containing 75 mole % hydrogen, an intermediate product stream that is predominantly methane and is a suitable fuel gas, and a heavy product stream that contains C2 to C5 components, the heavy components of the feed, which can be sold for fuel or as a chemical raw material or blended into fuel gas intermediate product stream. In this example, the heavy components are blended into the intermediate product fuel gas stream 48.

The dominant heavy component in the feed stream 10 is n-pentane. Accordingly, the solvent stream 20 is also rich in n-pentane, 37 mole % n-pentane. No external solvent is used; the solvent consists predominantly of heavy components derived from the feed.

The solvent inventory, accumulated in the flash drums, is maintained by controlling the temperatures at the outlet of the feed cooler 11, solvent cooler 18, and the intermediate product cooler 47 so that the heavy components in the feed going into the stripper absorber in stream 17 equals the heavy components in the light and intermediate product streams.

In this example, 99.8% of the hydrogen in the feed is recovered in the light product hydrogen rich stream 24A. A light product expander is not used because the hydrogen rich light product stream is delivered to its application at full absorber stripper pressure, so there is no pressure letdown.

TABLE 1

Typical Natural Gas Compositions

| | | Mol Percent | | |
|---|---|---|---|---|
| Component | Symbol | Associated Gas | Wet Gas | Dry Gas |
| Methane | $C_1$ | 27.52 | 59.52 | 97.17 |
| Ethane | $C_2$ | 16.34 | 5.36 | 1.89 |
| Propane | $C_3$ | 29.18 | 4.71 | 0.29 |
| i-Butane | $i\text{-}C_4$ | 5.37 | 2.03 | 0.13 |
| n-Butane | $n\text{-}C_4$ | 17.18 | 2.39 | 0.12 |
| i-Pentane | $i\text{-}C_5$ | 2.18 | 1.80 | 0.07 |
| n-Pentane | $n\text{-}C_5$ | 1.72 | 1.61 | 0.05 |
| Hexane | $C_6$ | 0.47 | 2.60 | 0.04 |
| Heptanes Plus | $C_{7+}$ | 0.04 | 19.98 | 0.24 |
| | | 100.00 | 100.00 | 100.00 |

TABLE 2

Sources of Hydrogen Off-Gas Streams

| Industry | Source | Approximate Hydrogen Concentration (Mol %) |
|---|---|---|
| Refining | HT Purge | 25–35 |
| | FCC Gas | 10–15 |
| | Cascade Reject | 50–60 |
| Methanol | Purge Gas | 70–80 |
| Ethylene | By-product $H_2$ | 60–90 |
| | Cracked Gas | 10–35 |
| Coke Oven | Product Gas | 0–5 |
| LPG Dehydrogenation | Product Gas | 58 |
| Toluene HDA | $H_2$ Purge | 57 |
| Cyclohexane | $H_2$ Purge | 42 |
| Carbon Black | Product Gas | 7 |
| Formaldehyde | By-product $H_2$ | 18 |
| Ammonia | Purge Gas | 60 |

TABLE 3

Example 1 (FIG. 2)
Natural Gas Nitrogen Rejection 40 MMSCFD Feed

| Stream Name | Feed | Feed Separator Bottoms/ Heavy Product | Feed Separator Overhead | Absorber Stripper Overhead | Light Product | First Flash Drum Overhead | First Flash Drum Bottoms |
|---|---|---|---|---|---|---|---|
| Stream Number (FIG. 1) | 10 | 14 | 17 | 24 | 29 | 33 | 34 |
| Temperature, °F. | 80 | −14 | −14 | −24 | 74 | −8 | −8 |
| Pressure, PSIA | 715 | 712 | 712 | 700 | 40 | 360 | 360 |
| Mass Flow, LB/HR | 97,770 | 6,638 | 91,132 | 39,917 | 36,104 | 43,770 | 1,014,347 |
| Gas Flow, MMSCFD | 40 | — | 38.66 | 12.13 | 11.96 | 22.04 | — |
| Liquid Flow, GPM | — | 23.56 | — | — | — | — | 3,165.04 |
| Composition, LB MOL/HR | | | | | | | |
| Helium | 3.95 | — | 3.95 | 3.94 | 3.94 | 0.04 | — |
| Nitrogen | 1,317.66 | 4.87 | 1,312.79 | 1,253.84 | 1,253.58 | 205.69 | 58.91 |
| $CO_2$ | 4.39 | 0.15 | 4.24 | 0.14 | 0.12 | 1.43 | 5.63 |
| Methane | 2,602.36 | 33.70 | 2,568.68 | 51.63 | 51.34 | 2,112.85 | 2,624.10 |
| Ethane | 256.51 | 20.04 | 236.47 | 10.63 | 4.63 | 56.33 | 564.88 |
| Propane | 106.73 | 26.47 | 80.26 | 5.78 | 0.09 | 21.71 | 1,004.52 |
| i Butane | 29.43 | 13.50 | 15.93 | 1.84 | — | 6.76 | 917.70 |

TABLE 3-continued

Example 1 (FIG. 2)
Natural Gas Nitrogen Rejection 40 MMSCFD Feed

| | | | | | | | |
|---|---|---|---|---|---|---|---|
| n Butane | 36.89 | 20.52 | 16.37 | 2.42 | — | 9.03 | 1,893.99 |
| i Pentane | 12.30 | 9.34 | 2.96 | 0.75 | — | 2.87 | 1,729.73 |
| n Pentane | 10.99 | 8.97 | 2.02 | 0.46 | — | 1.80 | 1,589.74 |
| n Hexane | 10.98 | 10.30 | 0.68 | 0.38 | — | 1.67 | 5,873.19 |
| TOTAL, LB MOL/HR | 4,392.20 | 147.85 | 4,244.35 | 1,331.83 | 1,313.71 | 2,420.17 | 16,262.39 |

| Stream Name | Second Flash Drum Overhead | Third Flash Drum Overhead | Fourth Flash Drum Overhead | Fourth Flash Drum Bottoms | Intermediate Product Separator Bottoms | Intermediate Product |
|---|---|---|---|---|---|---|
| Stream Number (FIG. 1) | 38 | 41 | 44 | 45 | 50 | 48 |
| Temperature, °F. | −11 | −19 | −24 | −20 | −9 | 120 |
| Pressure, PSIA | 245 | 70 | 20 | 20 | 444 | 815 |
| Mass Flow, LB/HR | 15,979 | 29,873 | 14,045 | 960,129 | 4865 | 55,03 |
| Gas Flow, MMSCFD | 8.16 | 14.23 | 5.3 | — | — | 26.7 |
| Liquid Flow, GPM | — | — | — | 2,837.71 | 17.47 | — |
| Composition, LB MOL/HR | | | | | | |
| Helium | 0.01 | — | — | — | — | 0.01 |
| Nitrogen | 39.51 | 18.37 | 1.48 | 0.08 | 0.15 | 59.21 |
| $CO_2$ | 0.67 | 2.15 | 1.41 | 1.52 | 0.11 | 4.12 |
| Methane | 808.81 | 1,347.82 | 384.45 | 107.51 | 23.74 | 2,517.34 |
| Ethane | 27.42 | 113.25 | 106.46 | 338.53 | 15.29 | 231.84 |
| Propane | 10.17 | 43.35 | 48.77 | 928.97 | 22.12 | 80.17 |
| i Butane | 300 | 11.71 | 13.32 | 903.10 | 12.10 | 15.93 |
| n Butane | 3.00 | 14.67 | 16.78 | 1,879.17 | 19.00 | 16.37 |
| i Pentane | 1.18 | 4.69 | 4.45 | 1,727.96 | 7.36 | 2.96 |
| n Pentane | 0.72 | 3.42 | 2.61 | 1,589.06 | 4.73 | 2.02 |
| n Hexane | 0.63 | 2.33 | 1.90 | 5,873.29 | 4.18 | 0.68 |
| TOTAL, LB MOL/HR | 896.05 | 1,561.76 | 581.62 | 13,349.19 | 108.78 | 2,930.65 |

TABLE 4

Example 2
Hydrogen Recovery (FIG. 2)
Overall Material Balance

| Stream | Feed | Light Product | Intermediate Product | Solvent |
|---|---|---|---|---|
| Stream Number | 10 | 24A | 48 | 20 |
| Temperature, °F. | 100 | 95 | 74 | −25 |
| Pressure, PSIA | 325 | 307 | 75 | 310 |
| Composition, LB-MOL/HR | | | | MOL % |
| Hydrogen | 1,103.02 | 1,100.41 | 2.60 | |
| Nitrogen | 108.89 | 90.56 | 18.33 | |
| $H_2S$ | 15.25 | 0.74 | 14.51 | |
| Methane | 3,255.13 | 213.54 | 3,041.59 | 1.01 |
| Ethane | 435.00 | 20.93 | 414.06 | 2.85 |
| Propane | 217.77 | 10.27 | 207.50 | 8.29 |
| i-Butane | 109.97 | 4.35 | 105.62 | 12.10 |
| n-Butane | 109.97 | 3.47 | 106.50 | 16.09 |
| i-Pentane | 42.47 | 1.28 | 41.18 | 22.59 |
| n-Pentane | 42.47 | 1.50 | 40.97 | 36.94 |
| TOTAL | 5,439.92 | 1,447.05 | 3,992.87 | |

What is claimed is:

1. A process for separating a feed gas stream consisting of components which have a spectrum of volatilities including most volatile (light) components, intermediate volatility components, and least volatile (heavy) components, comprising the steps of:

(a) cooling the feed gas stream in a feed gas cooler and separating a heavy component condensate form the feed gas;

(b) conveying a portion of the heavy component condensate produced in step (a) to an absorption zone, said portion of heavy component condensate being a liquid lean solvent;

(c) contacting the feed gas stream with the liquid lean solvent stream in the absorption zone to produce a light product gas stream and a rich solvent liquid stream so that the light product gas stream comprises the light components from the feed gas, and the rich solvent liquid stream comprises the lean solvent plus intermediate and heavy components that have been absorbed by the lean solvent in the absorption zone;

(d) flashing the rich solvent liquid stream form the absorption zone in a flashing zone to produce at lower pressure a flash gas stream and a lean solvent stream so that the flash gas (intermediate product) gas stream comprises the intermediate components form the feed gas, and the lean solvent consists essentially of heavy components supplied from the feed gas; and (e) conveying the lean solvent produced in step (d) to the absorption zone as the lean solvent stream in step (c).

2. The process of claim 1 comprising the additional step of:

(f) adjusting the temperature of the feed gas stream at the exit of the feed gas cooler in step (a) to maintain a specified inventory of lean solvent in the flash zone.

3. The process of claim 1 comprising the additional step of:

(f) conveying sufficient heavy component condensate into the flash zone to maintain a specified inventory of lean solvent in the flash zone.

4. The process of claim 1 comprising the additional step of:

(h) separating the condensed heavy product stream from the flash gas stream; and (i) conveying sufficient condensed heavy product produced in step (g) to the flash zone to maintain a specified inventory of lean solvent in the flash zone.

5. The process of claim 1 comprising the additional step of:

(f) compressing the flash gas (intermediate product) stream;

(g) cooling the compressed flash gas stream in an intermediate product cooler to condense a heavy product stream comprising heavy components;

(h) separating the condensed heavy product stream from the flash gas (intermediate product) stream; and (i) adjusting the temperature of the flash gas (intermediate product) stream at the exit of the intermediate product cooler in step (g) to maintain a specified inventory of lean solvent in the flash zone.

6. The process of claim 1 comprising the additional step of:

(f) cooling the lean solvent stream that is conveyed form the flash zone to the absorption zone in step (e) i a lean solvent cooler prior to feeding it into the absorption zone;

(g) controlling the temperature of the lean solvent stream leaving the lean solvent cooler; and (h) controlling the temperature of the lean solvent stream leaving the lean solvent cooler to maintain a specified inventory of lean solvent in the flash zone.

7. The process of claim 1 comprising the additional step of:

(f) cooling the light product gas stream by direct heat exchange, or by expansion, or by both direct heat exchange and expansion to condense a heavy product stream comprised of heavy components;

(g) separating the condensed heavy product stream from the light product stream; and (h) feeding sufficient condensed heavy product stream produced in step (g) into the flash zone to maintain a specified inventory of lean solvent in the flash zone.

8. The process of claim 1 wherein the feed gas is natural gas comprising nitrogen, methane and hydrocarbons heavier than methane; the light product stream consisting essentially of nitrogen; the intermediate product stream consisting essentially of methane; and the heavy product stream consisting essentially of hydrocarbons heavier than methane.

9. The process of claim 1 wherein the feed gas is petrochemical or refinery offgas comprising hydrogen, methane and hydrocarbons heavier than methane; the light product stream consisting essentially of hydrogen; the intermediate product stream consisting essentially of methane; and the heavy product stream consisting essentially of hydrocarbons heavier than methane.

10. The process of claim 9 further comprising the step of: conveying the light product stream produced in step (c) to a hydrogen purification unit in which the concentration of hydrogen in the light product stream is increased.

11. The process of claim 10 wherein the hydrogen purification unit is a pressure swing adsorption (PSA) unit.

12. The process of claim 1 wherein the feed gas is petrochemical or refinery offgas comprising hydrogen, nitrogen, methane and hydrocarbons heavier than methane; the light product stream consisting essentially of hydrogen and nitrogen; the intermediate product stream consisting essentially of methane; and the heavy product stream consisting essentially of hydrocarbons heavier than methane.

13. The process of claim 12 further comprising the step of: conveying the light product stream produced in step (c) to a hydrogen purification unit in which the concentration of hydrogen in the light product stream is increased.

14. The process of claim 13 wherein the hydrogen purification unit is a pressure swing adsorption (PSA) unit.

* * * * *

UNITED STATES PATENT AND TRADEMARK OFFICE
CERTIFICATE OF CORRECTION

PATENT NO. : 5,462,583        Page 1 of 4
DATED : OCTOBER 31, 1995
INVENTOR(S) : GLENN C. WOOD/YUV R. MEHRA It is certified that error appears in the above-indentified patent and that said Letters Patent is hereby corrected as shown below:

On the title page, under "Other Publications", please rewrite the first publication to read as follows:

--Szatny et al., "Field Test Performance Evaluation of the Mehra Process for Nitrogen Rejection from Natural Gas," Gas Research Institute, Topical Report (Feb. 1994), Houston, Tex., pp. 1-23.--

In col. 2, line 17, "ratio" should read --ratios--.

In col. 4, line 23, delete "is comprised of" and insert therefor --comprises--.

In col. 5, line 3, insert --the-- after "that".

In col. 6, line 60, delete "plan" and insert --diagram--.

In col. 7, line 44, delete "psi" and insert therefor --psia--.

In col. 11, line 61, delete "Inc." and insert therefor --in--.

In col. 11, line 62, delete "2" and insert therefor --12--.

In col. 12, line 39, insert a --"-- before "The".

UNITED STATES PATENT AND TRADEMARK OFFICE
CERTIFICATE OF CORRECTION

PATENT NO. : 5,462,583   Page 2 of 4
DATED : OCTOBER 31, 1995
INVENTOR(S) : GLENN C. WOOD/YUV R. MEHRA It is certified that error appears in the above-indentified patent and that said Letters Patent is hereby corrected as shown below:

In col. 14, line 1, delete "AICHE" and insert therefor --AIChE Spring--.

In col. 14, lines 5 and 9, delete "AICHE" and insert therefor --AIChE--.

In col. 14, line 30, please rewrite the publication to read as follows:

--"Field Test Performance Evaluation of the Mehra Process for Nitrogen Rejection from Natural Gas," Topical Report, 93/0448, Feb. 1994.--

In col. 14, line 33, insert a paragraph after "disclosed".

In col. 19, line 62, "-1,447.05" should read --1,447.05--.

In col. 20, line 16, delete "55,03" and insert therefor --55,031--.

Col. 20
In claim 1, lines 7, 21 and 25, delete "form" and insert therefor --from--.

In claim 1, line 23, insert --(intermediate product)-- after "gas".

In claim 1, line 26, insert --stream-- after "solvent".

UNITED STATES PATENT AND TRADEMARK OFFICE
CERTIFICATE OF CORRECTION

PATENT NO. : 5,462,583
DATED : OCTOBER 31, 1995
INVENTOR(S) : GLENN C. WOOD/YUV R. MEHRA

It is certified that error appears in the above-indentified patent and that said Letters Patent is hereby corrected as shown below:

Col. 21
In claim 4, line 1, insert an --s-- after "step".

In claim 4, line 3, please insert before "(h)":

--(f)    compressing the flash gas (intermediate product) stream;

(g)    cooling the compressed flash gas stream in an intermediate product cooler to condense a heavy product stream comprising heavy components;--

Col. 21
In claim 5, line 1, insert an --s-- after "step".

Col. 21
In claim 6, line 1, insert an --s-- after "step".

In claim 6, line 3, delete "form" and insert therefor --from--.

In claim 6, line 4, delete "i" and insert therefor --in--.

In claim 6, line 6, insert --and-- after "zone;".

In claim 6, lines 7-9, please delete

"controlling the temperature of the lean solvent stream leaving the lean solvent cooler; and (h)".

UNITED STATES PATENT AND TRADEMARK OFFICE
CERTIFICATE OF CORRECTION

PATENT NO. : 5,462,583—
DATED : OCTOBER 31, 1995
INVENTOR(S) : GLENN C. WOOD/YUV R. MEHRA

It is certified that error appears in the above-indentified patent and that said Letters Patent is hereby corrected as shown below:

Col. 21
In claim 7, line 1, insert an --s-- after "step".

Signed and Sealed this

Second Day of July, 1996

Attest:

BRUCE LEHMAN

Attesting Officer

Commissioner of Patents and Trademarks